United States Patent [19]
Andrews et al.

[11] Patent Number: 6,053,934
[45] Date of Patent: Apr. 25, 2000

[54] REPLACEABLE, MEDICAL DEVICE HANDLE

[75] Inventors: Marvin O. Andrews, Bloomington; Thomas L. Foster, Poland; Gerald J. French; Frederick D. Roemer, both of Bloomington, all of Ind.

[73] Assignee: Cook Urological, Incorporated, Spencer, Ind.

[21] Appl. No.: 09/088,908

[22] Filed: Jun. 2, 1998

Related U.S. Application Data

[60] Provisional application No. 60/048,293, Jun. 2, 1997.

[51] Int. Cl.$^7$ ..................................................... A61B 17/28
[52] U.S. Cl. ........................ 606/207; 606/206; 606/126; 600/104
[58] Field of Search .................................... 606/207, 206, 606/126, 127, 128, 113, 114, 115, 170, 171, 174, 200, 1; 600/104–108

[56] References Cited

U.S. PATENT DOCUMENTS

| | | |
|---|---|---|
| 4,592,341 | 6/1986 | Omagari et al. . |
| 4,733,662 | 3/1988 | DeSatnick et al. . |
| 4,791,913 | 12/1988 | Maloney . |
| 5,084,054 | 1/1992 | Bencini et al. ........................ 606/127 |
| 5,156,590 | 10/1992 | Vilmar . |
| 5,190,561 | 3/1993 | Graber ................................... 606/127 |
| 5,312,418 | 5/1994 | Bonnet ................................... 606/128 |
| 5,327,906 | 7/1994 | Fideler . |
| 5,333,603 | 8/1994 | Schuman . |
| 5,370,647 | 12/1994 | Graber et al. . |
| 5,386,817 | 2/1995 | Jones . |
| 5,433,725 | 7/1995 | Christian et al. . |
| 5,456,683 | 10/1995 | Fritzsch et al. . |
| 5,499,992 | 3/1996 | Meade et al. . |
| 5,507,772 | 4/1996 | Shutt et al. . |

Primary Examiner—Michael Buiz
Assistant Examiner—Lien Ngo
Attorney, Agent, or Firm—Richard J. Godlewski

[57] ABSTRACT

A replaceable handle (10) for side loading the proximal end of a medical device (41) therein, which is typically inserted with the operating lumen of an endoscope. The replaceable handle is easily removed from the proximal end of the medical device for removing an endoscope over the medical device. with the endoscope removed, the replaceable handle can side-load the proximal end of the device for added manipulation of the distal end such as in removing a stone from the kidney or ureter leading therefrom. the replaceable handle includes an outer elongated housing (11) with passage (13) extending longitudinally therein with external communication (14) therealong. The outer housing also includes a first attachment mechanism (15) disposed about the distal end for receipt of a first medical device member therein. The handle also includes an inner elongated member (17) positioned in the housing passage and extending proximally therefrom. A second attachment mechanism (19) is disposed in the inner elongated member and communicates with the housing passage for receipt therein of a second medical device member (20) adjacent the first member. The inner member also includes a positioning channel (18) in which a housing projection is positionable therein so as to control longitudinal and rotational movement of the inner member with respect to the outer housing. The inner elongated member is also rotatable for easily side-loading the proximal end of the medical device.

27 Claims, 2 Drawing Sheets

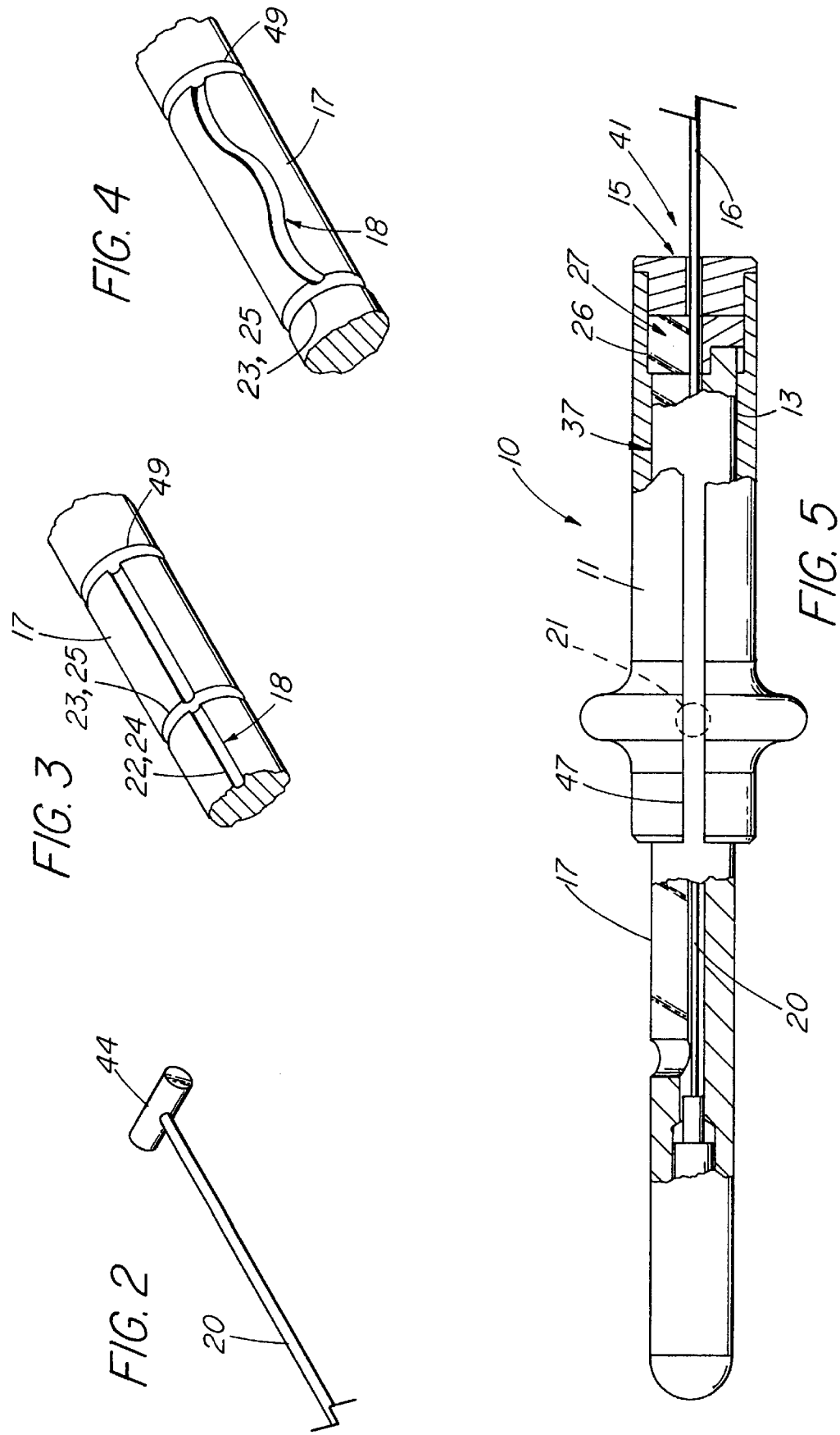

REPLACEABLE, MEDICAL DEVICE HANDLE

CROSS-REFERENCE TO RELATED APPLICATIONS

This application claims priority of provisional application Ser. No. 60/048,293, filed Jun. 2, 1997.

TECHNICAL FIELD

This invention relates generally to medical devices and, in particular, to a replaceable, side-loading handle for positioning the proximal end of a medical device therein.

BACKGROUND OF THE INVENTION

Extractors or baskets have been used for the removal of stones and other foreign objects from the urinary or biliary system. Often, the distal portion of these devices consist of a series of wires or strips that can be manipulated by the handle and actuating wire to expand to form an open basket. By further manipulating the handle of the extractor, the target object is captured within the basket, and the device is withdrawn from the body.

The procedure for extraction of a kidney stone usually requires that an endoscope be introduced to locate the obstruction. Once the stone is visualized, the basket or extractor is introduced through an operating lumen in the scope to complete the procedure. Occasionally, the extractor with the stone are too large to be safely withdrawn and further instrumentation such as forceps or an ultrasonic wire must be introduced that aid in fragmenting the object for removal. Without an additional operating lumen through which these instruments may be introduced, the endoscope must be withdrawn over the extractor. To accomplish this, the handle of the extractor must first be removed.

Handles for current extractors are end loaded with a hub or expanded portion at the proximal end of the actuating wires. The hubs locks into place with the handle mechanism. Unfortunately, however, they must be cut off the proximal end of the wire before the endoscope can be slid off the end of the extractor. This prevents reattachment and reuse of the handle to complete the procedure once the basket has been freed.

While handles have been developed that can be reused for subsequent medical procedures, none are known that can be used for situations as described above in which an endoscope can be readily removed and reintroduced during the same procedure without destruction of the actuating system. The ideal handle for a stone extractor must be able to be removed on a temporary basis and be easily reattached without the loss of handle function.

SUMMARY OF THE INVENTION

The foregoing problems are solved and a technical advance is achieved in an illustrative replaceable or removable side-loading handle for a medical device that is typically inserted through the operating lumen of an endoscope. The replaceable handle includes an outer elongated housing with a passage having external or lateral communication extending longitudinally at least partially therealong from the distal end thereof. Disposed preferably about the distal end of the housing is a first attachment mechanism that communicates with the housing passage for receipt of a first medical device member therein. This advantageously longitudinally positions the first medical device member in the side-loading handle. The handle also includes an inner elongated member positioned in the housing passage and preferably extending proximally therefrom and preferably having a positioning channel arrangement for advantageously controlling the longitudinal and the rotational or circumferential movement of the inner elongated member with respect to the outer housing. The inner elongated member also includes a second attachment mechanism disposed therein and communicating with the housing passage for receipt therein of a second medical device member adjacent the first member of the medical device. In the preferred embodiment, the first and second adjacent medical device members are coaxially positioned relative to each other so as to permit longitudinal as well as rotational movement. The outer housing also includes a projection positionable into the positioning channel of the inner elongated member to control longitudinal and rotational movement therebetween. The inner elongated member is longitudinally slidable in the housing passage when the housing projection is positioned in a longitudinal component of the positioning channel. The inner elongated member is also rotatable in the housing passage when the housing projection is positioned in a transverse or circumferential component of the positioning channel.

The housing projection advantageously extends into the positioning channel for controlling alternative longitudinal and rotational movement of the inner member with respect to the outer housing. The first attachment mechanism of the outer housing also includes a collar rotatably positioned in the passage about the distal end thereof. The collar can be characterized as a locking ring and includes a slit with external communication extending longitudinally therethrough and communicating with the passage of the outer housing. This advantageously provides for side loading of the medical device in the first attachment mechanism when the external communication slit is in alignment with the external communication slit of the outer housing. The collar also has an axially offset recess which mates with an axially offset projection extending distally from the inner elongated member. The offset projection is positioned in the offset recess of the collar for rotation of the collar in the housing passage when the inner elongated member is in a distal-most position in the housing passage. The first attachment mechanism also includes an end cap fixedly positioned in the housing passage and has a slit with external communication extending longitudinally therethrough and also communicating with the housing passage. The end cap and rotatable collar work in combination with each other to fixedly position the proximal end of a first medical device member side-loaded and positioned in the housing attachment mechanism.

The inner elongated member also advantageously includes an attachment mechanism comprising a passage extending longitudinally in the inner member and having external communication therealong and communicating with the housing passage. This also advantageously permits side loading of the proximal end of an other medical device member into the inner member of the replaceable handle and also fixedly positions the inner medical device member therein for longitudinal and rotational movement of the adjacent medical device members with respect to each other.

In another aspect, the invention provides a replaceable, medical device handle comprising:

an outer elongated housing having a distal end, a passage extending longitudinally therealong and having lateral communication thereto;

a first mechanism for attachment to a first medical device member when the latter is in said passage;

an inner elongated member positioned in said passage and extending therealong; and associated therewith a second mechanism for attachment to a second medical device member to be associated with the first medical device member, the outer housing and the inner member including a projection positionable in an associated channel arrangement to achieve relative rotational and longitudinal movement of the first and second device members. An extension can be provided for enabling relative movement of the inner member and the outer housing. The first mechanism can enable the first device member to be fixed relative to the outer housing, and the second mechanism can enable the second device member to be fixed relative to the inner member. Channels of the channel arrangement can be formed on the outer surface of the inner member, and the projection can be fixed to the outer housing and be arranged to be movable in the said channels.

BRIEF DESCRIPTION OF THE DRAWING

FIG. 2 depicts an alternative embodiment of the proximal end of the inner control rod member of the medical device of FIG. 1;

FIG. 3 depicts a partial pictorial view of another embodiment of the positioning channel in the inner elongated member of FIG. 1;

FIG. 4 depicts a partial pictorial view of a second alternative embodiment of the positioning channel disposed on the outer surface of the inner elongated member of FIG. 1; and FIG. 5 depicts a partially sectioned top view of the replaceable handle of the present invention with the proximal end of a medical instrument positioned and locked in the replaceable side-loading handle.

DETAILED DESCRIPTION

Figure 1:
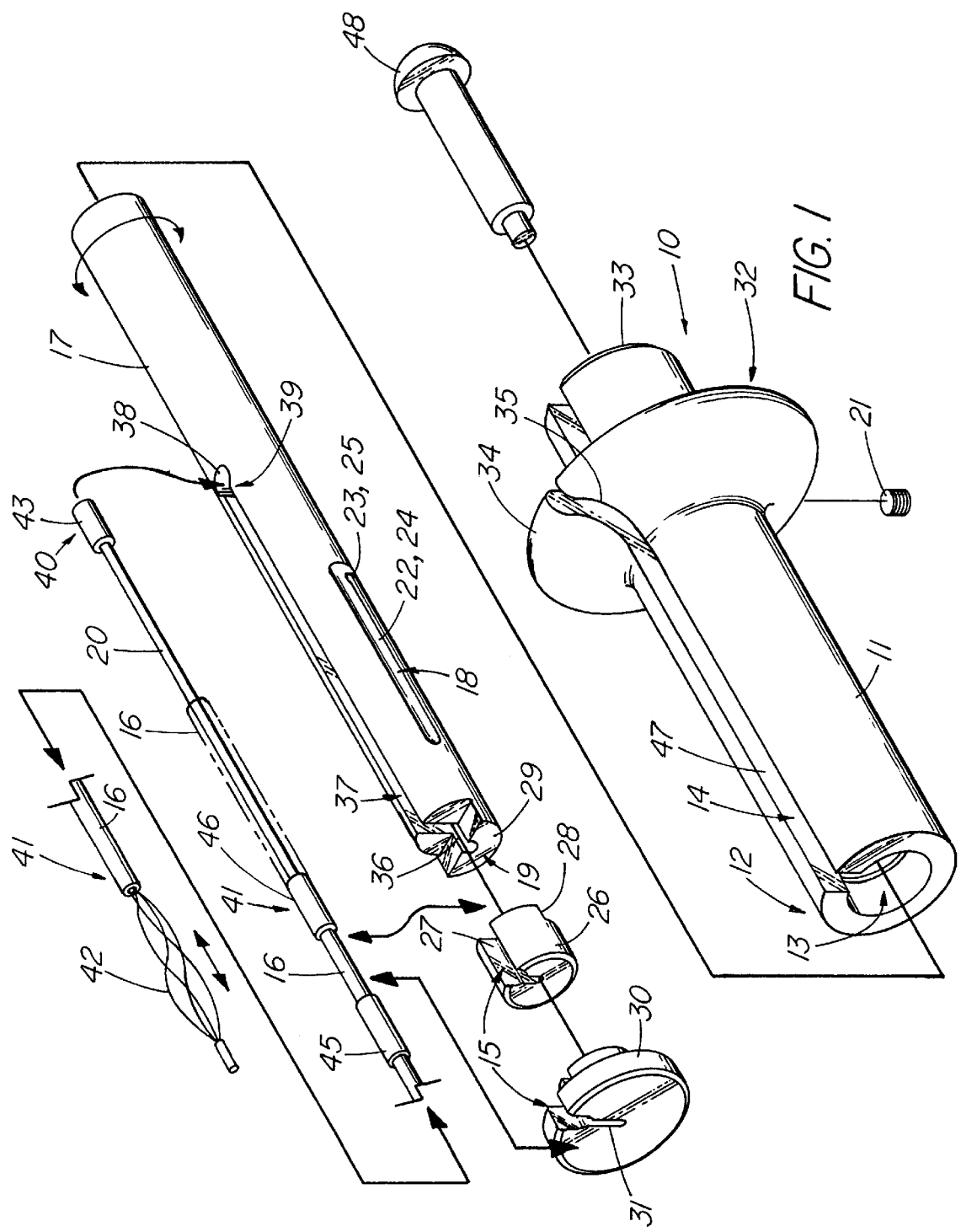
FIG. 1 depicts a pictorial assembly drawing of the present invention with a medical device shown in position for insertion into the side loading handle.

FIG. 1 depicts a preferred illustrative embodiment of replaceable handle 10 for medical device 41 such as stone basket 42, which is used to remove kidney stones or calculi from the calix of a patient's kidney or the ureter leading therefrom. The replaceable handle can likewise be utilized with other medical devices such as graspers, snares, retrievers, papillotomes, biopsy devices, occluders, tip deflecting wire guides, and other devices that are commonly used in conjunction with or through an operating lumen of an endoscope. Each of these medical devices is characterized in having at least two adjacent members at the proximal end thereof which are at least longitudinally and/or rotatably movable with respect to each other for the operation of the device at the distal end thereof. By way of example, medical device 41 depicted in FIG. 1 includes expandable spiral stone basket 42 at the distal end thereof, which is collapsible into outer sheath member 16 via relative longitudinal movement of inner control rod member 20. The control rod member is attached to stone basket 42 and controls the extension and withdraw of the stone basket from the distal end of outer sheath member 16. Since these endoscopic instruments are typically inserted through an operating lumen of an endoscope, the outer diameter of outer sheath member 16 typically ranges from 1.0 French up to and including 10 French (0.013 inches to 0.131 inches) with the preferred range being from 2.0 French to 5.0 French (0.026 inches to 0.066 inches).

Inner control rod member 20 extends through the passage of outer sheath member 16 and does not exceed the outer diameter of the outer sheath member except, for example, distal hub 43 or distal transverse cross member 44 (FIG. 2), which does not exceed the inner diameter of an endoscope lumen through which the medical device is passed therethrough.

The replaceable medical device handle of the present invention advantageously provides for easy side loading of the proximal end of a medical device and fixation thereto. Existing handles typically require longitudinal attachment of the medical device to the handle through one or more small end holes. This side-loading feature is a convenience to the physician and is readily appreciated, particularly, when a grasper or stone basket can not be operated to release the captured stone, tissue sample or other device fragment. Should the captured stone become unreleasable, replaceable handle 10 can be easily removed from the proximal end of the medical device so as to permit the endoscope to be removed from the patient and passed over the proximal portion of the medical device. This advantageously eliminates the destructive removal of the handle or an enlarged proximal end from the medical device prior to removal of the endoscope therearound. The replaceable handle 10 is then easily reattached to the proximal end of the medical device for subsequent operation and removal of the medical device by the attending physician.

Replaceable, medical device handle 10 includes outer elongated housing 11 having passage 13 extending longitudinally therethrough in which inner elongated member 17 is slidably positioned in the passage and extends proximally therefrom. Outer elongated housing 11 includes distal end 12 of which a first attachment mechanism 15 such as distal end cap 30 is disposed about the distal end. The first attachment mechanism 15 including distal end cap 30 communicates with outer housing passage 13 for receipt and positioning of outer sheath member 16 therein. The end cap includes a multiple width slit 31 with external communication extending longitudinally therethrough and communicating with outer housing passage 13. The end cap slit extends to the center thereof for side loading and positioning of outer sheath member 16 therein between distal and proximal sleeves 45 and 46 positioned around outer sheath member 16 and longitudinally spaced to receive end cap 30 and locking ring collar 26 therebetween.

Passage 13 of outer elongated housing 11 has external communication 14 such as longitudinal slit 47 extending longitudinally therealong for advantageously side loading the proximal end of medical device 41 therethrough. By way of example, outer elongated housing 11 is formed from a Delrin plastic material having a tubular shape approximately 2.500 inches long with annular flange extending radially therefrom disposed approximately 0.5500 inches from the proximal end thereof. The annular flange has an outer diameter of approximately 0.9478 inches with the main tubular portion of the housing having an outer diameter of approximately 0.5500 inches. Outer housing passage 13 has a minimum inner diameter of approximately 0.3760 inches extending therethrough, which is counter-bored to a depth of approximately 0.4500 inches from the distal end thereof to receive and position locking ring collar 26 and end cap 30 therein. Longitudinal slit 47 has a width of approximately 0.0937 inches which extends the entire length of outer housing 11. The longitudinal slit also extends through flange 34 and forms flange slit 35 for, again, advantageous side loading and passage of the proximal end of medical device 41 therethrough. In addition, outer elongated housing 11 includes a projection 21 that is radially inserted through flange 34 and extends into housing passage 13 and positioning channel 18 of inner elongated member 17. In this preferred embodiment, a 6–32 hole is drilled and tapped radially through flange 34 and into passage 13. Projection 21 is a set screw that is positioned in the drilled and tapped hole and extends into passage 13 and inner member positioning channel 18. Alternatively, projection 21 can be a spring loaded piston or rod that transversely extends into passage 13 and is manually withdrawn by the attending physician to withdraw inner elongated member 17 from passage 13 of outer housing 11. Alternatively, flange 32 can comprise one or more radially extending tabs that are positioned longitudinally thereapart for positioning the finger or thumb of the physician therein. As a result, a complete annular flange is not required as well as flange slit 35.

First attachment mechanism 15 also includes locking ring collar 26 longitudinally positioned in the distal end of passage 13 as previously described with collar slit 27 extending radially from the center thereof and communicating with longitudinal passage 13 and longitudinal slit 47. Distal end cap 30 is fixedly positioned in the distal end of outer housing 11 with end cap slit 31 communicating with longitudinal slit 47 of the housing. Locking ring collar 26 is fixedly positioned longitudinally in passage 13 but is rotatable therein to circumferentially surround outer sleeve member 16 therein when inner elongated member 17 engages collar 26 and rotates it in outer housing passage 13. To facilitate rotation thereof, collar 26 includes axially offset recess 20 which mates with axially offset projection 29 of inner elongated member 17. When the offset recess and projection are mated with each other, rotation of inner elongated member 17 in turn rotates collar 26 to circumferentially surround and lock outer sheath member 16 therein. Rotation of the inner elongated member from a locked positioned will align collar slit 27 and inner member passage 36 with outer housing slit 47 for removal of the medical device from replaceable handle 10.

In the preferred embodiment, inner elongated member 17 is cylindrical in shape and is formed from a Delrin plastic material. The overall length of the inner member is approximately 4.3125 inches with an outer diameter of approximately 0.3750 inches. Second attachment mechanism 19 includes passage 36 disposed in the inner member and extending proximally from the distal end thereof, which communicates with housing passage 13 for the receipt therein of at least a second medical device member such as control rod member 20. Passage 36 extends radially from inner member 17 and longitudinally from the distal end for approximately 3.0 inches. The width of passage 36 is approximately 0.0625 inches. To longitudinally position inner control rod member 20 and distal hub 43, second attachment mechanism 19 also includes transversely enlarged recess 38, which is disposed about and externally communicating with proximal end 39 of inner member passage 36. Transverse recess 38 is enlarged to receive enlarged proximal end 40 of inner control rod member 20 such as cylindrical proximal sleeve or hub 43 fixedly attached thereto. Inner member passage 36 also includes external communication 37 which includes the previously described slit for receipt and side loading of at least second control rod member 20 therethrough and into inner member passage 36. Alternatively, the proximal end of inner control rod member 20 depicted in FIG. 2 can include transverse cross member 44 which is positioned in enlarged recess 38.

The transverse cross member locks the control rod member in enlarged recess 38 of the second attachment mechanism for rotation of inner control rod member 20 with respect to outer sheath member 16. Enlarged recess 38 has a major diameter of approximately 0.2000 inches and a minor diameter of approximately 0.1560 inches and extends from the surface of the inner member to passage 36 extending longitudinally therethrough. For ease of manufacture and assembly, passage 36 extends longitudinally through inner member 17. A proximal end cap 48 is positioned in the proximal end of passage 36 and securely fastened therein using, for example, medical grade adhesive.

Inner elongated member 17 also includes positioning channel 18 formed in the surface thereof for longitudinally and rotationally positioning the inner member in outer elongated housing 11. The positioning channel includes a longitudinal component 22 as well as a rotational or circumferential component 23. Housing projection 21 that extends into housing passage 13 also extends or is extendable into positioning channel 18 and longitudinal and rotational components 22 and 23. When the housing projection is positioned in longitudinal component 22 of the positioning channel, inner elongated member 17 is longitudinally slideable in housing passage 13 for longitudinal operation of outer sheath member 16 and inner control rod member 20 with respect to each other. In this particular embodiment, the longitudinal movement of the inner and outer members of the medical device causes stone basket 42 to be extended and withdrawn from the distal end of outer sheath member 16.

When housing projection 21 is positioned in the rotational or circumferential component 23 of positioning channel 18, inner elongated member 17 can be rotated with respect to outer housing 11 to radially align external communication slit 14 and external communication slit 37 with each other to side load or remove the proximal end of medical device 41 therein or therefrom. In the side-load or unlocked position, the proximal end of medical device 41 is passed through external communication slit 47 of housing 11 and external communication slit 37 of inner elongated member 17. In addition, outer sheath member 16 is positioned in first attachment mechanism 15 and, in particular, through cap slit 31 of distal end cap 30 and collar slit 27 of collar 26 between distal and proximal outer sheath sleeves 45 and 46. When medical device 41 is positioned in the first and second attachment mechanisms of the outer housing and inner elongated member, inner member 17 is rotated in housing passage 13 with housing projection 21 in rotational component 23 of positioning channel 18. This rotational movement of the inner and outer members causes external communication slits 14 and 37 to become radially misaligned, thus locking the proximal end of medical device 41 in replaceable handle 10.

To facilitate rotational movement, locking ring collar 26 includes axially offset recess 28 extending in from the proximal end thereof. By way of example, the locking ring collar is generally cylindrical in shape, with a length of approximately 0.2500 inches with an outer diameter of approximately 0.3870 inches. Collar slit 27 extends from the center thereof to the outer surface to provide external communication with outer external communication slit 47 and inner communication slit 37. To facilitate easy side loading of the proximal end of the medical device, collar slit 27 is approximately 0.0626 inches wide to a depth of 0.1145 inches. The collar slit extends through the center of the collar with a narrowed width of approximately 0.033 inches. Offset collar recess 28 is diametrically opposed from the collar slit to a depth of 0.1250 inches and likewise recessed an equal amount from the proximal end thereof. To engage the collar recess, inner elongated member 17 includes an axially offset projection 29 extending distally and longitudinally therefrom. Offset projection 29 is positionable in collar offset recess 28 when positioned therein when the inner member is positioned in the distal-most portion of housing passage 13. As previously indicated, locking ring collar 26 is fixedly positioned longitudinally in housing passage 13. However, when inner elongated member 17 is in the distal-most position and housing projection 21 in rotational component 23 of positioning channel 18, the inner elongated member is allowed to rotate, with locking ring collar 26 following suit due to the engagement of collar offset recess 28 and inner member offset projection 29.

FIG. 3 depicts an alternative embodiment of positioning channel 18 disposed in an outer surface of inner elongated member 17. In this embodiment, the positioning channel includes radial components 23 and 49 that extend at least partially around the circumference of inner elongated member 17. When inner elongated member 17 is slid to a distal-most position in outer housing 11, collar offset recess 28 and inner member offset projection 29 engage each other to permit the rotation and locking of medical device 41 in replaceable handle 10. In this situation, housing projection 21 is positioned in second rotational component 49 of the positioning channel. When the inner elongated member is slid proximally with housing projection 21 in longitudinal component 22 to first rotational component 23, inner elongated member can be rotated with respect to outer housing 11, likewise rotating inner control rod member 20 with respect to outer sheath member 16. During this rotational movement, since offset recess 28 and offset recess projection 29 are disengaged from each other, locking ring collar 26 remains in a locked positioned maintaining outer sleeve member 16 in first attachment mechanism 15 of the outer housing.

FIG. 4 depicts a second alternative embodiment of positioning channel 18 disposed in the outer surface of inner elongated member 17. In this particular embodiment, the positioning channel has a serpentine configuration for a side-to-side motion of the inner member with respect to the outer housing as the inner member is longitudinally moved relative to the outer housing. This serpentine configuration includes both a longitudinal and a circumferential component. Separate rotational component 23 and 49 can be included in the surface of inner elongated member 17 to provide for rotational movement of locking collar 26 as well as rotational movement of the inner elongated member with the locking collar in a locked position with outer sheath member 16 enclosed therein.

FIG. 2 depicts an alternative embodiment of inner control rod member 20 with transverse cross member 44 fixedly attached to the proximal end thereof. As indicated, this particular configuration permits the inner control rod to not only be longitudinally operated with respect to outer sheath member 16, but also permits rotation therebetween with transverse cross member fixedly positioned in enlarged recess 38 of attachment mechanism 19.

FIG. 5 depicts a partially sectioned top view of replacement handle 10 with the proximal end of medical device 41 inserted therein. Inner elongated member 17 is positioned in housing passage 13 of outer elongated member housing 11. In this particular configuration, locking ring collar 26 has been rotated in housing passage 13 such that external communication slit 37 and collar slit 27 are misaligned with external communication slit 47, thereby locking outer sheath member 16 in first attachment mechanism 15.

Housing projection 21 extends into longitudinal component 22 of positioning channel 18 to permit the longitudinal movement of the inner elongated member 17 with respect to outer housing 11 as well as outer sheath member 16 with respect to inner control rod member 20.

It is to be understood that the above-described replaceable medical device handle is merely an illustrative embodiment of the principles of the invention and that other side-loading handles may be devised by those skilled in the art without departing from the spirit and scope of this invention. It is contemplated that first attachment mechanism 15 has been described with a locking ring collar 26. However, it is contemplated that locking ring collar 26 of the attaching mechanism can be eliminated along with mating offset projection 29 on inner elongated member 17. In this particular configuration, the distal and proximal sleeves 45 and 46 need to be moved forward distally on outer sheath member 16. As a result, the proximal end of outer sheath member 16 will extend into inner member passage 36 regardless of its longitudinal position in housing passage 36. As long as the outer sheath member 16 extends into inner member passage 36, the opportunity for the proximal end of the medical device to laterally flex or move out of first and second attachment members 15 and 19 is minimized, if not eliminated. As also previously suggested, housing projection 21 can be spring loaded to extend only into housing passage 13, when desired. With this embodiment, positioning channel 18 can assume any number of different configurations with a multitude of longitudinal and rotational or circumferential components.

What is claimed is:

1. A replaceable, medical device handle (10) comprising:
    an outer elongated housing (11) having a distal end (12), a passage (13) extending longitudinally therein and having external communication (14) therealong, and a first attachment mechanism (15) disposed about said distal end and communicating with said passage for receipt of a first medical device member (16) therein; and
    an inner elongated member (17) positioned in said passage and extending proximally therefrom and having a positioning channel (18), a second attachment mechanism (19) disposed therein and communicating with said passage for receipt therein of a second medical device member (20) adjacent the first medical device member, said outer elongated housing also including a projection (21) positionable into said positioning channel, said inner elongated member being longitudinally slidable in said passage when said projection is positioned in a first component (22) of said positioning channel and being rotatable in said passage when said projection is positioned in a second component (23) of said positioning channel.

2. The handle of claim 1, wherein said first component of said positioning channel comprises a longitudinal segment (24) of said positioning channel and wherein said second component of said positioning channel comprises a lateral segment (25) of said positioning channel.

3. The handle of claim 1, wherein said projection extends into said positioning channel.

4. The handle of claim 1, wherein said first attachment mechanism includes a collar (26) rotatably positioned in said passage about said distal end of said outer elongated housing and having a slit (27) with external communication extending longitudinally therethrough and communicating with said passage.

5. The handle of claim 4, wherein said collar also has an offset recess (28) and wherein said inner elongated member includes an offset projection (29) extending distally and longitudinally therefrom and positionable in said offset recess of said collar for rotation of said collar in said passage.

6. The handle of claim 1, wherein said first attachment mechanism comprises a cap (30) fixedly positioned about said distal end of said outer elongated housing and having a slit (31) with external communication extending longitudinally therethrough and communicating with said passage.

7. The handle of claim 6, wherein said first attachment mechanism includes a collar (26) rotatably positioned in said passage about said distal end of said outer elongated housing and having a slit (27) with external communication extending longitudinally therethrough and communicating with said passage.

8. The handle of claim 1, wherein said outer elongated housing includes at least one flange (32) disposed about a proximal end (33) and extending radially therefrom.

9. The handle of claim 8, wherein said at least one flange comprises an annular flange (34) having a slit (35) with external communication extending longitudinally therethrough and communicating with said passage.

10. The handle of claim 1, wherein said second attachment mechanism comprises a passage (36) extending longitudinally in said inner member and having external communication (37) therealong and communicating with said passage of said outer elongated housing.

11. The handle of claim 10, wherein said second attachment mechanism further comprises an enlarged recess (38) disposed about and externally communicating with a proximal end (39) of said external communication (37) to receive an enlarged proximal end (40) of the second adjacent device member.

12. A replaceable, medical device handle (10) comprising:

an outer elongated housing (11) having a distal end (12), a passage (13) extending longitudinally therealong and having external communication (14) thereto;

a first mechanism (15) for attachment to a first medical device member (16) when said first medical device member is in said passage;

an inner elongated member (17) having an outer surface, said inner elongated member positioned in said passage and extending therealong; and associated therewith a second mechanism (19) for attachment to a second medical device member (20) to be associated with the first medical device member, the outer housing and the inner member including a projection (21) positionable in a positioning channel (18) formed on an outer surface of said inner member, said positioning channel including a first component and a second component to achieve relative rotational and longitudinal movement of the first and second device members.

13. A handle according to claim 12, wherein an extension is provided for enabling relative movement of the inner member and the outer housing.

14. A handle according to claim 13, wherein the first mechanism enables the first medical device member to be fixed relative to the outer housing, and the second mechanism enables the second device member and to be fixed relative to the inner member.

15. A handle according to claim 12, wherein channels of the channel arrangement are formed on the outer surface of the inner member, and the projection is fixed to the outer housing and is arranged to be movable in the said channels.

16. A handle according to claim 13, wherein channels of the channel arrangement are formed on the outer surface of the inner member, and the projection is fixed to the outer housing and is arranged to be movable in the said channels.

17. A handle according to claim 14, wherein channels of the channel arrangement are formed on the outer surface of the inner member, and the projection is fixed to the outer housing and is arranged to be movable in the said channels.

18. The handle of claim 12, wherein said first component of said positioning channel comprises a longitudinal segment (24) of said positioning channel and wherein said second component of said positioning channel comprises a lateral segment (25) of said positioning channel.

19. The handle of claim 12, wherein said projection extends into said positioning channel.

20. The handle of claim 12, wherein said first attachment mechanism includes a collar (26) rotatably positioned in said passage about said distal end of said outer elongated housing and having a slit (27) with external communication extending longitudinally therethrough and communicating with said passage.

21. The handle of claim 20, wherein said collar also has an offset recess (28) and wherein said inner elongated member includes an offset projection (29) extending distally and longitudinally therefrom and positionable in said offset recess of said collar for rotation of said collar in said passage.

22. The handle of claim 12, wherein said first attachment mechanism comprises a cap (30) fixedly positioned about said distal end of said outer elongated housing and having a slit (31) with external communication extending longitudinally therethrough and communicating with said passage.

23. The handle of claim 22, wherein said first attachment mechanism includes a collar (26) rotatably positioned in said passage about said distal end of said outer elongated housing and having a slit (27) with external communication extending longitudinally therethrough and communicating with said passage.

24. The handle of claim 12, wherein said outer elongated housing includes at least one flange (32) disposed about a proximal end (33) and extending radially therefrom.

25. The handle of claim 24, wherein said at least one flange comprises an annular flange (34) having a slit (35) with external communication extending longitudinally therethrough and communicating with said passage.

26. The handle of claim 12, wherein said second attachment mechanism comprises a passage (36) extending longitudinally in said inner member and having external communication (37) therealong and communicating with said passage of said outer elongated housing.

27. The handle of claim 26, wherein said second attachment mechanism further comprises an enlarged recess (38) disposed about and externally communicating with a proximal end (39) of said external communication (37) to receive an enlarged proximal end (40) of the second adjacent device member.

* * * * *